United States Patent [19]

Wolfer et al.

[11] 4,262,664

[45] Apr. 21, 1981

[54] ORTHOPEDIC KNEE DEVICE

[76] Inventors: Adolf Wolfer, Neckarstr. 189, 7000 Stuttgart - 1, Fed. Rep. of Germany; Hans R. Lehneis, 255 W. Shore Dr., Massapegua, N.Y. 11758

[21] Appl. No.: 876,727

[22] Filed: Feb. 10, 1978

[30] Foreign Application Priority Data

Feb. 12, 1977 [DE] Fed. Rep. of Germany ....... 2705978

[51] Int. Cl.³ .............................................. A61F 3/00
[52] U.S. Cl. .................................. 128/80 C; 128/88
[58] Field of Search ............... 128/80 C, 80 R, 80 F, 128/88, 87; 2/22, 24

[56] References Cited

U.S. PATENT DOCUMENTS

| 2,558,986 | 7/1951 | Seelert | 128/80 F |
| 2,559,473 | 7/1951 | Slodek, Sr. | 128/80 F |
| 3,026,869 | 3/1962 | Peach | 128/80 F |
| 3,669,105 | 6/1972 | Castiglia | 128/80 C |

FOREIGN PATENT DOCUMENTS 2724586 12/1978 Fed. Rep. of Germany ........ 128/80 C

Primary Examiner—John D. Yasko

[57] ABSTRACT

A knee brace for the prevention of over-stretching of the knee has two guide rails, one on each side of the knee, two cross members or straps to connect the respective ends of the two guide rails to contact the front of the thigh and the calf, and a cross member resting against the hollow of the knee and effecting the locking action. The cross member conforms to the contour of the thigh, and is formed of a firm material, is hinged to the two lateral guide rails.

9 Claims, 3 Drawing Figures

ORTHOPEDIC KNEE DEVICE

BACKGROUND OF THE INVENTION

The present invention relates to a knee brace or orthesis to prevent over-stretching of the knee.

Such knee braces are generally known and in use. For instance, in an article entitled "The Swedish Knee Cage", published in the journal "Artificial Limbs", Vol. 12, No. 2, pages 54–57, Fall 1968, a knee brace is described which consists of two lateral guide rails, one each on either side of the knee and interconnected by several straps and clamps. The upper and lower ends of the guide rails, respectively, are connected by a strap. The straps themselves or the retaining loops attached to them are riveted to the guide bars and the strap rests against the front of the thigh and the calf, the correct contact of the straps being achieved through adjustment of their length by means of snap fasteners, on the one hand, and by the deformability of the straps, on the other hand.

At the level of the knee joint, the two rails are interconnected firmly by a semi-circular, rigid cross member and a cushion which supports itself against the hollow of the knee, thus preventing the knee from over-stretching.

This embodiment is considered disadvantageous in that the contact made by the straps in front of the thigh and the calf is incorrect or non-existent, particularly when the knee is bent. This can cause the knee brace to shift, and in addition, place the projecting straps so that they are outlined in an undesirable manner through the clothing—pants or skirt—so as to be clearly visible.

It is an object of the invention to provide a knee brace for the prevention of over-stretching of the knee, consisting essentially of two guide rails, one on each side of the knee, two cross members or straps to connect the respective ends of the two guide rials and to contact the front of the thigh and the calf, and a cross member resting against the hollow of the knee and effecting the locking action. The brace assures a perfect fit from both functional and cosmetic aspects.

SUMMARY OF THE INVENTION

According to the invention, this problem is solved in that the cross member resting against the thigh conforms to the contour of the thigh is formed of a firm material and is hinged to the two lateral guide rails.

According to one embodiment of the invention, a strap hugging the back of the thigh is attached to the cross member in contact with the thigh.

The flexibility of the cross member hugging the thigh is achieved with particular ease in that the strap is fastened at two opposite points of the cross member which is spaced at a predetermined distance from the hinge connections between the cross member and the two lateral guide rails.

Other details and advantages of the invention may be learned from the specification below and from the annexed drawings.

BRIEF DESCRIPTION OF THE DRAWINGS

In the accompanying figures.

DESCRIPTION OF THE INVENTION

Figure 1:
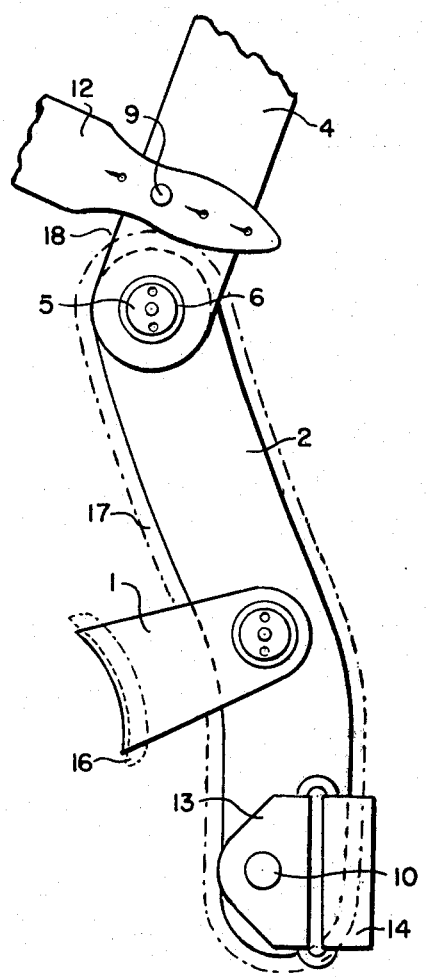
FIG. 1 is a side view of the knee brace.

The knee brace comprises a pair of generally vertically disposed guide rails 2, which are adapted to extend above and below the patient's knee joint to follow the general contour of the leg in intimate contact therewith. The guide rails are slightly S-shaped and have a bluge 3. An upper cross member 4, hugging the thigh is pivotably connected at the upper ends of the rail to extend across the front of the patient's thigh. A medial cross member 1 is also pivotably mount-intermediate the ends of the rails to extend across the rear of the patient's leg below the knee joint. A further strap 11 is located at the lower end to extend across the front of the leg calf.

The strap 11, in contact with the front of the calf, is adjustable in known manner. For this purpose, it is permanently attached to one guide rail 2, while its other end is held in a strap fastening 13 with a buckle 14. According to one expedient embodiment of this knee brace, a slide lock is provided to permit adjustable locking in a continuous length. This has the additional advantage of easy manipulation. The upper ends of the guide rails 2 are interconnected by the cross car 4, designed and fastened in accordance with the invention, and resting against the front of the thigh.

Figure 2:
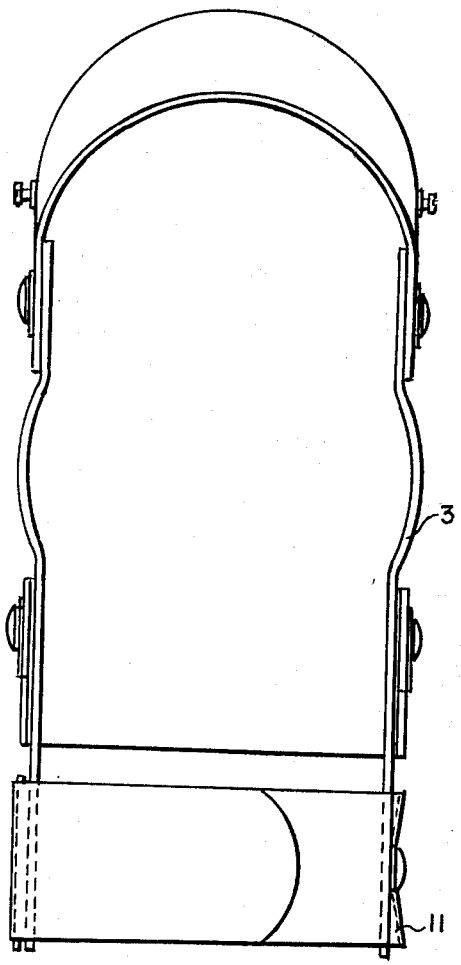
FIG. 2 is a front view of the knee brace.

Both FIGS. 1 and 2 make it clear that the cross bar 4, consisting of a firm material, essentially conforming to the contour of the knee, also taking into account the shape of the guide rails 2.

The selection of the specific material for cross member 4 is largely left to the discretion of the specialist, the stiffness and strength required being determined by the function, while the aspects of convenience in wearing and inconspicuousness are governing for dimension and shape. In one prototype, for instance, a plastic-coated light-metal material has proven very useful.

Figure 3:
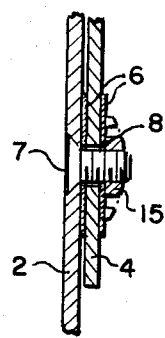
FIG. 3 is an enlarged view of the hinge connection.

So that the cross bar 4 continues to hug the thigh when the knee is bent, such as in a sitting position, the cross member 4 and the guide rails 2 are joined to each other by a hinge connection 5. For stability reasons, i.e., in order to make the hinge connection 5 strong enough at minimum structural height, the parts movable relative to each other are separated from each other by large area sliding discs 6, a bearing sleeve 8 being pushed over the hinge screw as seen in FIG. 3. As illustrated in the embodiment shown, a strap 12, extending along the back of the thigh, supports the cross member 4, and insures that it makes continuous contact with the thigh. To maintain the greatest possible flexibility and simplicity of handling, the strap 12 is buttoned on both sides into ball head screws 9 provided at a distance from the hinge connection 5.

Cushions 16, 17, and 18 are used for convenience of the wearer.

It is evident from FIG. 1, in particular, that in the knee brace according to the invention, the medial cross member 1, located in the hollow of the knee, is also fastened to the guide rails 2 by means of a hinge connection. This also contributes to greater flexibility, yet firm seating, which is possible otherwise in the known knee braces, for instance, only within the scope of the deformability of the straps or the cushioning. The bulge 3 in FIG. 2 indicates that the guide bars 2 conform to the contour of the leg.

For quick release and simple, stepless adjustability, the strap 12 may also be provided with a slide lock buckle.

FIG. 3 shows in larger scale one embodiment of the hinge connection 5. A flat head hinge screw 7 is put into an appropriate hole from the inside of the guide rail 2, so that the screw head does not protrude. A sleeve 8 is pushed over the hinge screw 7 on the outside of the guide rail 2. Large area sliding discs 6 are provided between the guide bar 2 and the clasp 4, as well as between the latter and the nut 15 forming the counterbearing.

We claim:

1. A brace for application on a patient's leg to stabilize the knee joint and prevent knee strain, comprising:
    a pair of opposed rigid guide rails constructed and arranged to extend above and below the patient's knee joint on either side of his leg;
    an upper cross-member mounted near the top of each guide rail and positioned to extend across the front of the patient's thigh;
    a medial cross-member mounted to each of said guide rails intermediate its ends and extending across the rear of the patient's leg in the vicinity of the knee joint; and
    a lower cross member mounted to each of said guide rails near the lower end thereof and positioned to extend across the patient's shin;
    at least one of said cross-members being at least partially detachable to permit application and removal of the knee brace on the patient's leg, at least one of said upper end medial cross-members being mounted for pivotal movement with respect to said guide rails so that said at least one cross-member pivots to conform said knee brace to the patient's leg as he bends and extends the same.

2. A knee brace in accordance with claim 1 wherein said guide rails are shaped to follow the general profile of the patient's leg.

3. A knee brace in accordance with claim 1 wherein said guide rails are fitted in intimate contact at the sides of the patient's leg, thereby providing lateral stabilization of the knee joint.

4. A knee brace in accordance with claim 3 wherein said guide rails bow outwardly and away from the patient's leg in the vicinity of the knee joint and are thereby adapted to accomodate a swelled joint.

5. A knee brace in accordance with claim 1 wherein said upper cross-member is shaped to conform to the contour of the front of the patient's thigh and is mounted for pivotal movement with respect to each of said guide rails.

6. A knee brace in accordance with claim 1 wherein said medial cross-member is shaped to conform to the contour of the rear of the patient's leg in the vicinity of the knee joint and is mounted for pivotal movement with respect to said guide rails.

7. A knee brace in accordance with claim 1 wherein said lower cross-member is detachable to permit application and removal of said knee brace.

8. A knee brace in accordance with claim 7 wherein said lower cross-member is a flexible strap, at least one of said guide rails having a strap-receiving loop mounting said strap thereto, said strap extending through said loop and being fastened so as to fold back on itself to secure the brace on the patient's leg, said strap including releasable means for retaining said strap in its folded back position.

9. A knee brace in accordance with claim 1 wherein the cross-member which is pivotally mounted with respect to said guide rails is mounted thereto by means of a hinge joint corresponding to each of said guide rails, each hinge joint comprising:
    shaft means extending through the corresponding guide rail and said cross member;
    first and second slide discs mounted on said shaft means to be coaxial therewith and having large surface areas, the first slide disc being disposed between the corresponding guide rail and said cross-member, the second slide disc being disposed on the opposite side of one of said corresponding guid rail and said cross-member, said slide discs serving to stabilize the corresponding guide rail and cross-member during pivotal movement; and
    means for retaining said shaft means and slide discs against linear movement with respect to the corresponding guid rail and said cross-member.

* * * * *